US008543419B2

(12) United States Patent  (10) Patent No.: US 8,543,419 B2
Reed  (45) Date of Patent: Sep. 24, 2013

(54) METHODS, SYSTEMS, AND COMPUTER PROGRAM PRODUCTS FOR PROVIDING AN INFORMATION STORAGE MANAGEMENT SYSTEM

(75) Inventor: Paul Reed, Brookline, MA (US)

(73) Assignee: International Business Machines Corporation, Armonk, NY (US)

( * ) Notice: Subject to any disclaimer, the term of this patent is extended or adjusted under 35 U.S.C. 154(b) by 871 days.

(21) Appl. No.: 11/961,552

(22) Filed: Dec. 20, 2007

(65) Prior Publication Data

US 2009/0164246 A1     Jun. 25, 2009

(51) Int. Cl.
*G06Q 10/00* (2012.01)

(52) U.S. Cl.
USPC .................................................. 705/3; 705/2

(58) Field of Classification Search
USPC ............................................................. 705/3
See application file for complete search history.

(56) References Cited

U.S. PATENT DOCUMENTS

| 6,383,135 | B1 * | 5/2002 | Chikovani et al. | 600/300 |
| 6,524,241 | B2 * | 2/2003 | Iliff | 600/300 |
| 6,607,482 | B1 * | 8/2003 | Teitelbaum | 600/300 |
| 7,583,861 | B2 * | 9/2009 | Hanna et al. | 382/305 |
| 2006/0101055 | A1 | 5/2006 | Valdiserri et al. | |
| 2006/0178569 | A1 | 8/2006 | Dean | |

* cited by examiner

*Primary Examiner* — Hiep V Nguyen
(74) *Attorney, Agent, or Firm* — Cantor Colburn LLP; Louis Percello

(57) ABSTRACT

Methods, systems, and computer program products for providing a policy-based information storage management system for digital assets are provided. The storage management system includes multiple physical storage subsystems, each with deterministic storage characteristics. A method includes receiving a data item related to a subject and looking up a record for the subject. The record identifies corresponding digital assets that are stored in the storage subsystems. The method also includes applying a policy to the corresponding digital assets based upon the data item. The method further includes determining a subset of the digital assets in the record that are relevant to the data item. The relevance determination is made in response to application of the policy. The method also includes migrating the relevant digital assets to at least one designated storage subsystem, based upon corresponding storage characteristics, for expediting access to the relevant digital assets.

19 Claims, 4 Drawing Sheets

METHODS, SYSTEMS, AND COMPUTER PROGRAM PRODUCTS FOR PROVIDING AN INFORMATION STORAGE MANAGEMENT SYSTEM

BACKGROUND OF THE INVENTION

The present disclosure relates generally to data storage systems and, in particular, to methods, systems, and computer program products for providing a policy-based information storage management system in a medical-related environment.

Digital record keeping processes, for example, those servicing the medical field are driven by digital imaging technology, which has recently seen a tremendous growth. For example, in the field of medicine, as new imaging technologies emerge, the amount of digitized data for a given patient gets bigger and bigger. For example, there now exists a 256-slice CT scanner that produces high-resolution, three-dimensional images of a human body in under a minute. The amount of data collected in a single scan is huge and provides vital information for a treating clinician. Digital imaging has become a critical element in the diagnosis and treatments of patients.

The storage requirements for such data can increase exponentially with these advancements in scanner and digital data collection technology. As the volume of data increases, so do the storage requirements for housing this data. Since immediate access to the data is critical to patient care, many facilities find that keeping these large data sets instantly available to a treating clinician becomes more difficult, as their information technology (IT) storage systems reach capacity. This can lead to operational problems and system failures, or worse, compromise patient care.

Traditional computer environments seek to partition this data, such that selected data sets are stored in fast access memory and others are relegated to slower, long-term memory (e.g., magnetic tape). However, determining which data sets to store in each of the storage systems is not always easily ascertained.

What is needed, therefore, is a policy-driven information storage management system and process that determines which data sets are stored in rapidly accessible storage subsystems and which data sets are stored in slower storage subsystems.

BRIEF SUMMARY OF THE INVENTION

Embodiments of the invention include methods for providing a policy-based information storage management system for digital assets. The storage management system includes multiple physical storage subsystems, each with deterministic storage characteristics. A method includes receiving a data item related to a subject and looking up a record for the subject. The record identifies corresponding digital assets that are stored in the storage subsystems. The method also includes applying a policy to the digital assets based upon the data item. The method further includes determining a subset of the digital assets in the record that are relevant to the data item. The relevance determination is made in response to application of the policy. The method also includes migrating the relevant digital assets to at least one designated storage subsystem, the designation based on the corresponding storage characteristics, for expediting access to the relevant digital assets for medical data.

Additional embodiments include systems for providing a policy-based information storage management for digital assets. The storage management system includes multiple physical storage subsystems, each with deterministic storage characteristics. A system includes a computer processing device in communication with the storage subsystems. The system also includes an information storage management application executing on the computer processing device. The information storage management application implements a method. The method includes receiving a data item related to a subject and looking up a record for the subject. The record identifies corresponding digital assets that are stored in the storage subsystems. The method also includes applying a policy to the digital assets based upon the data item. The method further includes determining a subset of the digital assets in the record that are relevant to the data item. The relevance determination is made in response to application of the policy. The method also includes migrating the relevant digital assets to at least one designated storage subsystem, based upon the corresponding storage characteristics, for expediting access to the relevant digital assets for medical data.

Further embodiments include computer program products for providing a policy-based information storage management system for digital assets. The storage management system includes multiple physical storage subsystems, each with deterministic storage characteristics. A computer program product includes instructions for causing a computer to implement a method. The method includes receiving a data item related to a subject and looking up a record for the subject. The record identifies corresponding digital assets that are stored in the storage subsystems. The method also includes applying a policy to the digital assets based upon the data item. The method further includes determining a subset of the digital assets in the record that are relevant to the data item. The relevance determination is made in response to application of the policy. The method also includes migrating the relevant digital assets to at least one designated storage subsystem, based upon corresponding characteristics, for expediting access to the relevant digital assets for medical data.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

In accordance with exemplary embodiments, a policy-driven information storage management system and process are disclosed. The information storage management system and processes utilize policies which, upon implementation, determine which data sets of the system are stored in a particular physical storage subsystem. In an exemplary embodiment, the policies to be applied are related to a medical condition, symptoms, and/or diagnosis of a patient, as will be described further herein.

Figure 1:
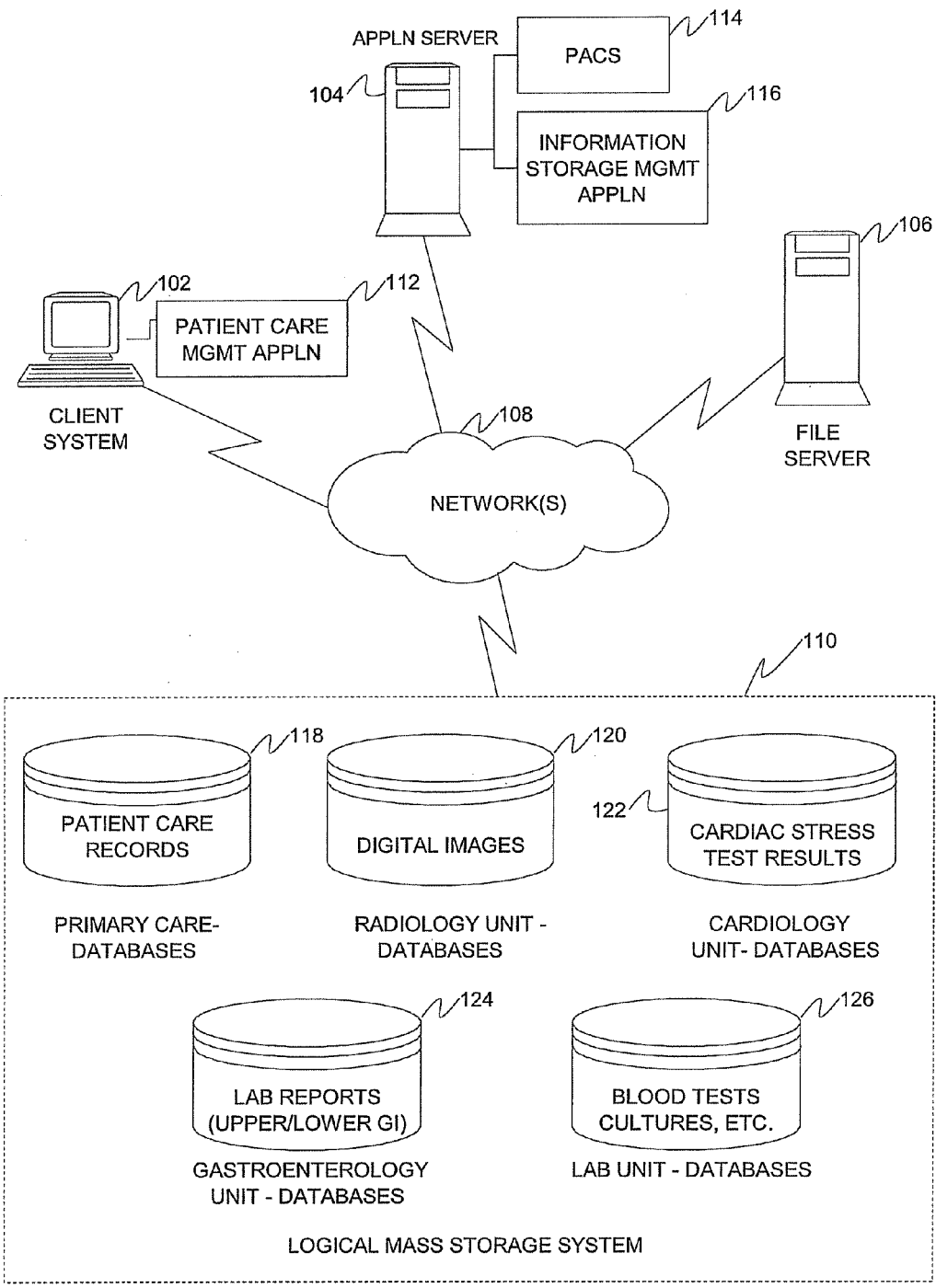
FIG. 1 depicts a block diagram of a system upon which information storage management processes may be implemented in accordance with exemplary embodiments.

Turning now to FIG. 1, an exemplary system upon which information storage management processes maybe implemented will now be described. The system of FIG. 1 may be directed to a hospital or medical facility, or a group of such facilities, which are communicatively coupled via a networked environment. Referring to FIG. 1, a client system 102, application server 104, and file server 106 are in communication with one or more networks 108. Also in communication with the networks 108 is a single logical mass storage system 110.

The client system 102 may be implemented using a general-purpose computer executing a computer program for carrying out various processes associated with a medical facility. The client system 102 may be a personal computer (e.g., a lap top, a personal digital assistant) or a host-attached terminal. If the client system 102 is a personal computer, the processing described herein may be shared by the client system 102 and the application server 104 (e.g., by providing an applet to the client system 102). Alternatively, the client system 102 may be a remote system operating over a wireless network (e.g., one of networks 108). The client system 102 executes a patient care management application 112 for entering data (e.g., symptoms; personal information, such as age, gender, insurance; date of examination/treatment, etc.). The client system 102 may reside in a medical facility (emergency room admissions or testing unit) or may be remotely located (e.g., a handheld device or vehicle communications component operated by an emergency medical technician (EMT)). An operator of the client system 102 enters the patient data into the system 102, which is used by the information storage management processes as described herein.

In alternative embodiments, the system of FIG. 1 may include multiple client systems 102 through which users at one or more geographic locations may contact the application server 104. The client systems 102 may be coupled to the application server 104 via the networks 108.

The application server 104 executes computer instructions for performing the information storage management processes. In an exemplary embodiment, the application server 104 executes an information storage management application 116. Additionally, the application server 104 executes a PACS (Picture Archiving and Communications Systems) system 114 or similar software as is typically found in the radiology department of a medical facility. The file server 106 may operate as a network file server to communicate with the client system 102. The file server 106 retrieves data files from the storage system 110 and presents the data files to requesting client systems, such as client system 102.

The networks 108 may be any type of known networks including, but not limited to, a wide area network (WAN), a local area network (LAN), a global network (e.g. Internet), a virtual private network (VPN), and an intranet. The networks 108 may be implemented using a wireless network or any kind of physical network implementation known in the art. A client system 102 may be coupled to the servers 104/106 through multiple networks (e.g., intranet and Internet) so that not all client systems 102 are coupled to the servers 104/106 through the same network. In one embodiment, the client system 102 may be connected directly (i.e., not through the networks 108) to the servers 104/106 and the servers 104/106 may be connected directly to or contain the storage system 110.

The storage system 110 includes data repositories with databases relating to medical information and may be implemented using a variety of devices for storing electronic information. It is understood that the storage system 110 may be implemented using memory contained in one or more servers (e.g., servers 104/106) or that it may be comprised of separate physical devices. The storage system 110 is logically addressable as a consolidated data source across a distributed environment that includes networks 108. Information stored in the storage system 110 may be retrieved and manipulated via the application server 104 and/or via the client system 102. The storage system 110 includes one or more databases containing medical data. The medical data in the databases may be text or binary coming from a variety of sources, such as, but not limited to, applications running on computer terminals within the facility (both manual data entry and automated through dictation), medical image scanners, or from other facilities over a WAN.

As shown in FIG. 1, there are six databases of information: primary care databases 118, radiology unit databases 120, cardiology unit databases 122, gastroenterology unit databases 124, and lab unit databases 126. These databases 118-126 are shown for illustrative purposes. It will be understood that other types of databases may be employed by the information storage management processes of the invention. The storage system of FIG. 1 stores information from the databases 118-126 in varying types of physical storage devices (e.g., cache level, random access memory, disk/tape drive, etc.). The information storage management processes implement one or more policies for determining in which physical storage device the data are housed.

The policy used to determine how to manage the data within the storage domain may be driven by clinical diagnosis or similar information in real time. In one embodiment, data is collected (also referred to as data items) for a subject (patient) via a medical dictation session, which is recorded on a computerized dictation device. The information storage management processes perform a text-based analysis on the data items, whereby the data items conform to a common medical nomenclature. The analysis includes determining aspects of the various digital assets that match those of the data items. In another embodiment, the information storage management processes utilize pre-defined policies which are applied to digital assets associated with the subject, resulting in a subset of the digital assets for storage in each storage subsystem. These features will now be described further in FIGS. 2 and 3.

As indicated above, the storage system 110 includes one or more physical storage subsystems. At step 302, a data item related to a subject (e.g., patient) is received via the patient care management application 112. The data item may be patient personal data, patient symptoms, and/or patient diagnoses. The personal data may include information such as age, gender, occupation, insurance, etc., of the patient.

The information storage management application 116 looks up a record for the subject at step 304. The record stores patient medical data. It will be understood that the patient medical record may be one typically found in a medical facility. The record identifies corresponding digital assets associated with the patient that are stored in the storage subsystems (110). The digital assets may include results of tests, such as MRIs, CT scans, ultrasounds, x-rays, and lab work (blood tests, cultures, etc.).

At step 306, a policy is applied to the digital assets based upon the data item, and a subset of the digital assets in the record which are relevant to the data item are ascertained at step 308. In one embodiment, the data item includes a symptom of a condition, wherein the policy comprises a minimum number of a group of symptoms related to a diagnosis. The data item may also include a date acknowledged for a symptom, condition, or diagnosis; wherein the policy comprises a pre-defined range of dates. Further the data item may include a severity value assigned to a symptom, wherein the policy comprises a minimum threshold of the severity value.

Figure 2:
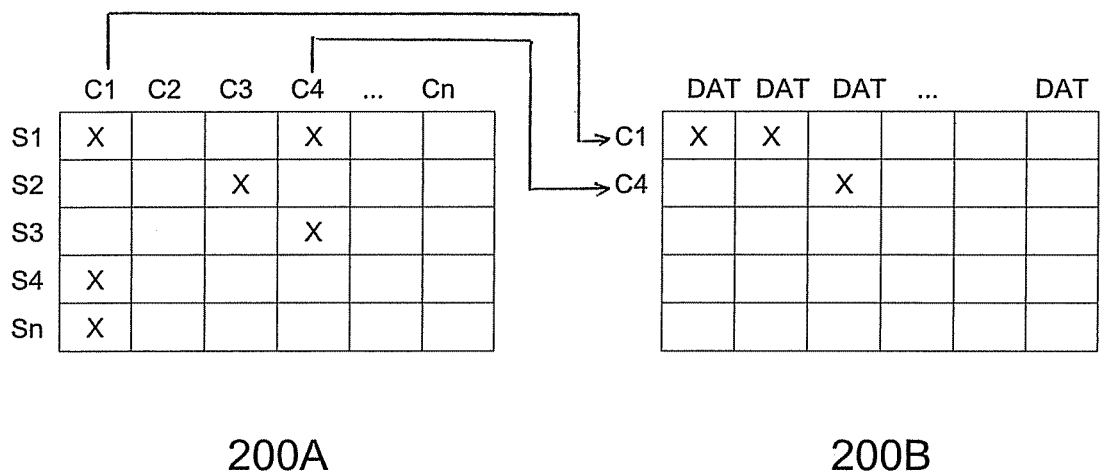
FIG. 2 is a sample policy used in implementing information storage management process in accordance with exemplary embodiments.
Figure 3:
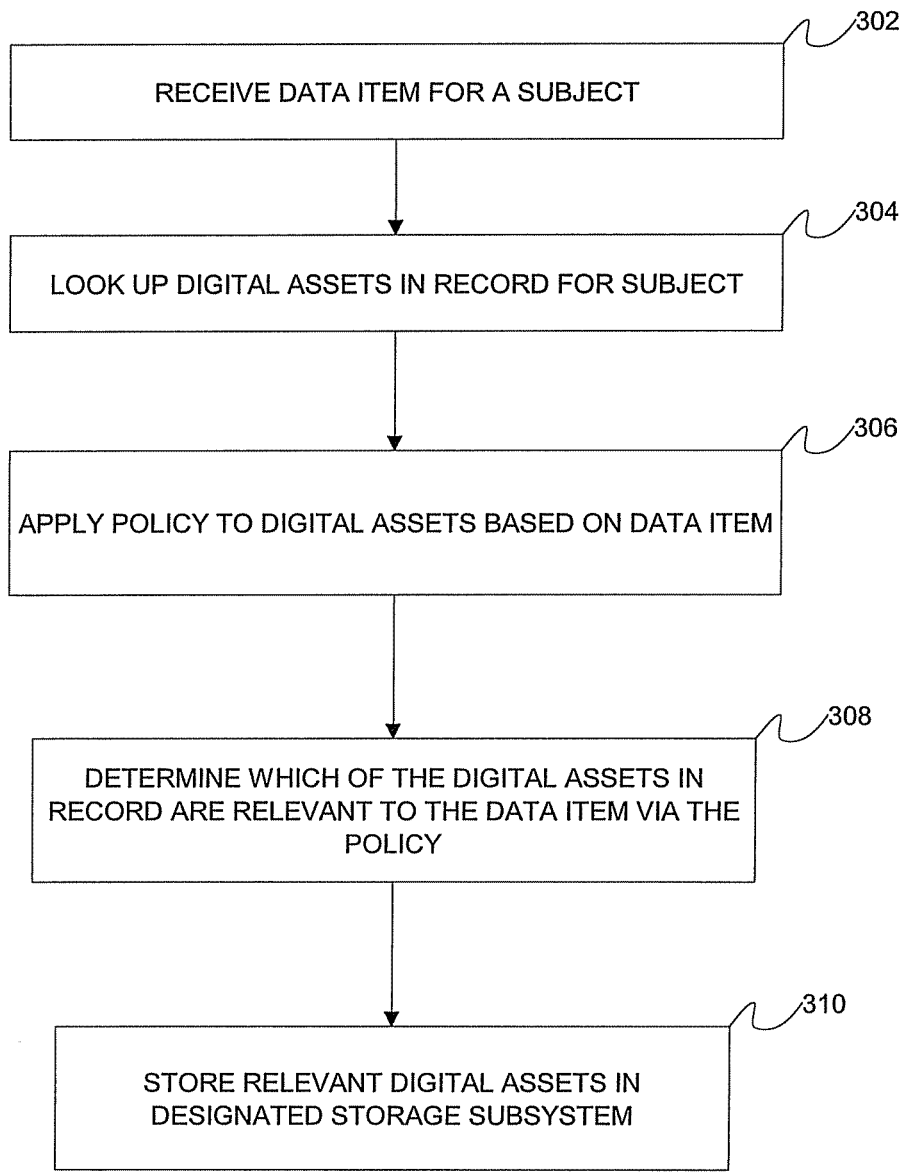
FIG. 3 is a flow diagram describing a process for implementing information storage management processes in accordance with exemplary embodiments.

As shown in FIG. 2 an exemplary policy is applied in which collected data items (S1, S4, and Sn), which reflect symptoms for a matrix 200A, correspond to one or more potential diagnoses or conditions (C1 and C4), which are then mapped to digital asset types (DAT) in matrix 200B. The digital asset types may reflect types of testing (e.g., MRI, CT scan, x-ray), as well as specifics of the testing, such as x-ray of the wrist. Thus, using the digital assets stored in the databases 118-126 of FIG. 1, a patient who is presenting with angina may have had tests previously performed, which correspond to the data asset types associated with these databases 118-126. Accordingly, the information storage management application 116 may identify one or more digital assets in response to application of the policy.

Figure 4:
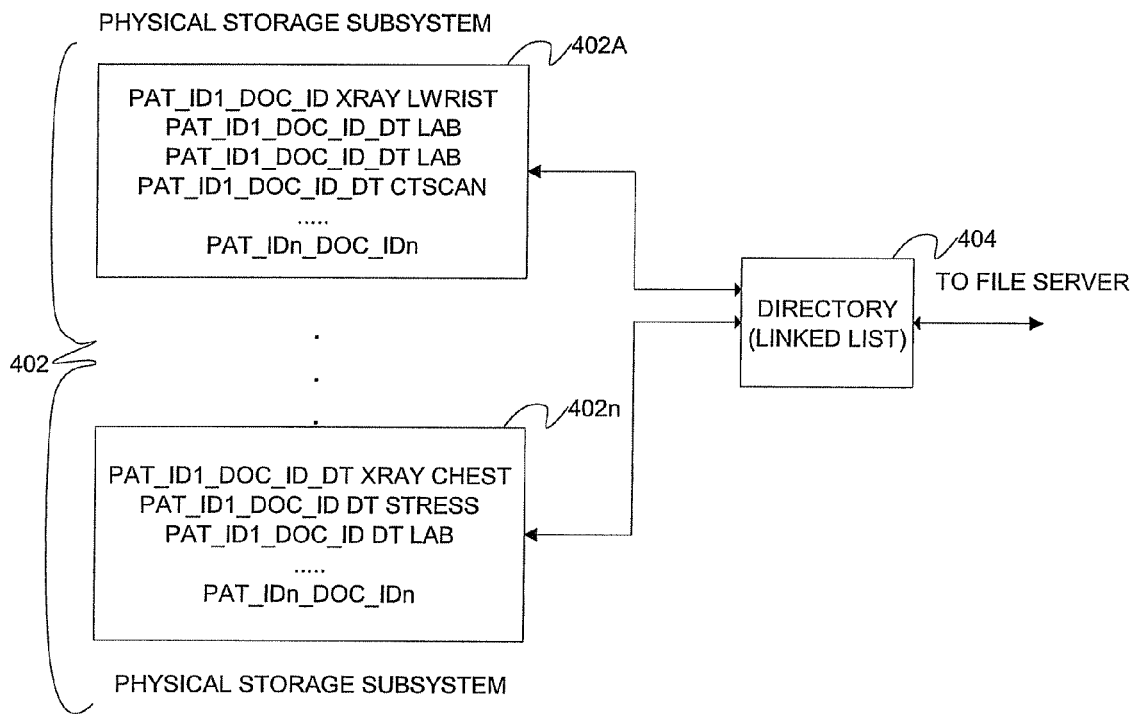
FIG. 4 is a hierarchical storage system illustrating results of an implementation of the information storage management processes with respect to a sample set of data items.

At step 310, the relevant digital assets are migrated to the appropriate storage subsystem for expedited access by the clinician. The appropriate storage subsystem may be determined based upon its corresponding storage characteristics, such as speed, access method, location, availability, etc. In one exemplary embodiment, the appropriate storage subsystem is one that offers high-speed access (such as, RAM). As shown in FIG. 4, e.g., a spectrum of storage subsystems include storage subsystem 402A (e.g., slowest-access storage of the facility, such as magnetic tape) through storage subsystem 402n (e.g., fastest-access memory) store various digital assets resulting from application of the policy. A directory 404 may be used to track which assets are stored in which subsystem. The storage subsystems 402A through 402n collectively house various portions of the databases 118-126 of FIG. 1.

In another embodiment, the data item may comprise a mass casualty and the policy comprises a storage plan for digital assets using storage capacities and locations associated with the physical storage devices.

In a further embodiment, the data item is collected during a medical examination session via a medical dictation device. The subset of the digital assets may be determined by parsing a dictation session comprising the data item and mapping the data item to corresponding digital assets in the record.

In yet a further embodiment, storage of the relevant digital assets in the storage subsystem is performed by identifying a portion of at least one of the relevant digital assets that includes a feature of interest to a clinician and partitioning the digital asset that includes the feature into segments. A segment that contains the feature is stored in a selected storage subsystem (e.g., rapid-access storage such as 402n), and remaining segments of the digital asset are stored one or more storage subsystems 402A-402n-1, as shown in FIG. 4, for example.

In imaging fields (e.g., radiology), where a study comprises multiple images, or slices, representing a 3D or 4D view of the patient, there is the potential to tag slices, groups of slices, and/or features within those slices a particular study. In another embodiment, a clinician identifies features in PACS system 114 (e.g., spot, shadow) and the slices in which those features are identified. The information storage management processes break down the digital asset into smaller digital assets and store the segmented digital asset containing the features of interest in a rapid access storage subsystem (e.g., 402n). The remaining segmented portions of the digital asset may continue to be stored on the slower-access storage subsystems. In this manner, the relevant slices are made immediately available to the clinician.

As described above, embodiments can be embodied in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:
1. A method, comprising:
providing, via a computer processor, matrices of symptoms and corresponding conditions, wherein selected groupings of the symptoms and the corresponding conditions are mapped from the matrices to digital asset types, the digital asset types representing types of diagnostic testing performed for the corresponding conditions;

receiving a data item related to a patient, the data item comprising at least one of the symptoms from the matrices;

looking up a record for the patient via the computer processor, the record identifying digital assets for the patient that are stored in the storage subsystems;

applying, via the computer processor, a policy to the digital assets using the matrices and based upon the data item, the policy defining a minimum number of a group of the symptoms related to a diagnosis;

selecting a subset of the digital assets in the record, the subset selected responsive to the applying the policy; and migrating, via the computer processor, the subset of the digital assets to at least one designated storage subsystem, based upon corresponding storage characteristics, operable for expediting access to the subset of the digital assets;

wherein the data item further includes a severity value assigned to the symptom, and the policy comprises a minimum threshold of the severity value.

2. The method of claim 1, wherein the record stores patient medical data and the data item further includes at least one of:
patient personal data; and
patient diagnoses.

3. The method of claim 1, wherein the digital assets include at least one of a(n):
MRI;
CT scan;
Ultrasound;
x-ray; and
lab test results.

4. The method of claim 1, wherein the data item further includes a date acknowledged for the symptom;
wherein the policy comprises a pre-defined range of dates.

5. The method of claim 1, wherein the data item further includes a mass casualty and the policy comprises a storage plan for digital assets using storage capacities associated with the storage subsystems.

6. The method of claim 1, wherein receiving the data item includes collecting data from a medical examination session via a medical dictation device, and
wherein the selecting a subset of the digital assets in the record includes parsing a dictation session comprising the data item and mapping the data item to corresponding digital assets in the record.

7. The method of claim 1, wherein determining a subset of the digital asserts includes:
identifying a portion of at least one of the subset of the digital assets that includes a feature of interest to a clinician, the feature specifying an aspect of a health condition captured in the at least one of the subset of the digital assets; and
partitioning the digital asset that includes the feature into segments;
wherein migrating the subset of the digital assets to a designated one of the storage subsystems includes storing the segment that contains the feature in the designated storage subsystem and storing remaining segments of the digital asset in another storage subsystem that has slower access time than the designated storage subsystem.

8. A system, comprising:
a computer processing device in communication with storage subsystems; and an information storage management application executing on the computer processing device, the information storage management application implementing a method, comprising:
providing matrices of symptoms and corresponding conditions, wherein selected groupings of the symptoms and the corresponding conditions are mapped from the matrices to digital asset types, the digital asset types representing types of diagnostic testing performed for the corresponding conditions;

receiving a data item related to a patient, the data item comprising at least one of the symptoms from the matrices;

looking up a record for the patient, the record identifying digital assets for the patient that are stored in the storage subsystems;

applying a policy to the digital assets using the matrices and based upon the data item, the policy defining a minimum number of a group of the symptoms related to a diagnosis;

selecting a subset of the digital assets in the record, the subject selected responsive to the applying the policy; and migrating the subset of the digital assets to at least one designated storage subsystem, based on corresponding storage characteristics, operable for expediting access to the subset of the digital assets;

wherein the data item further includes a severity value assigned to the symptom, and the policy comprises a minimum threshold of the severity value.

9. The system of claim 8, wherein the record stores patient medical data and the data item further includes at least one of:
patient personal data; and
patient diagnoses.

10. The system of claim 8, wherein the digital assets include at least one of a(n):
MRI;
CT scan;
Ultrasound;
x-ray; and
lab test results.

11. The system of claim 8, wherein the data item further includes a date acknowledged for the symptom;
wherein the policy comprises a pre-defined range of dates.

12. The system of claim 8, wherein the data item further includes a mass casualty and the policy comprises a storage plan for digital assets using storage capacities associated with the storage subsystems.

13. The system of claim 8, wherein receiving the data item includes collecting data from a medical examination session via a medical dictation device, and
wherein the selecting a subset of the digital assets in the record includes parsing a dictation session comprising the data item and mapping the data item to corresponding digital assets in the record.

14. A computer program product comprising a non-transitory computer-readable storage medium having instructions embodied thereon, which when executed by a computer, causes the computer to implement a method, the method comprising:
providing matrices of symptoms and corresponding conditions, wherein selected groupings of the symptoms and the corresponding conditions are mapped from the matrices to digital asset types, the digital asset types representing types of diagnostic testing performed for the corresponding conditions;

receiving a data item related to a patient, the data item comprising at least one of the symptoms from the matrices;

looking up a record for the patient, the record identifying digital assets for the patient that are stored in the storage subsystems;

applying a policy to the digital assets using the matrices and based upon the data item, the policy defining a minimum number of a group of the symptoms related to a diagnosis;

selecting a subset of the digital assets in the record, the subset selected responsive to the applying the policy; and migrating the subset of the digital assets to at least one designated storage subsystem, based on corresponding storage characteristics, operable for expediting access to the subset of the digital assets;

wherein the data item further includes a severity value assigned to the symptom, wherein the policy comprises a minimum threshold of the severity value.

15. The computer program product of claim 14, wherein the record stores patient medical data and the data item further includes at least one of:
 patient personal data; and
 patient diagnoses.

16. The computer program product of claim 14, wherein the digital assets include at least one of a(n):
 MRI;
 CT scan;
 Ultrasound;
 x-ray; and
 lab test results.

17. The computer program product of claim 14, wherein the data item further includes a date acknowledged for the symptom;
 wherein the policy comprises a pre-defined range of dates.

18. The computer program product of claim 14, wherein the data item further includes a mass casualty and the policy comprises a storage plan for digital assets using storage capacities associated with the storage subsystems.

19. The computer program product of claim 14, wherein receiving the data item includes collecting data from a medical examination session via a medical dictation device, and
 wherein the selecting a subset of the digital assets in the record includes parsing a dictation session comprising the data item and mapping the data item to corresponding digital assets in the record.

\* \* \* \* \*